United States Patent [19]

Mirviss et al.

[11] 4,378,320

[45] Mar. 29, 1983

[54] META-TERTIARY-BUTYLPHENYL DIPHENYL PHOSPHATE

[75] Inventors: Stanley B. Mirviss, Stamford, Conn.; Silvio L. Giolito, Whitestone, N.Y.

[73] Assignee: Stauffer Chemical Company, Westport, Conn.

[21] Appl. No.: 204,967

[22] Filed: Nov. 7, 1980

Related U.S. Application Data

[62] Division of Ser. No. 91,633, Nov. 5, 1979, Pat. No. 4,280,945.

[51] Int. Cl.³ .............................................. C07F 9/09
[52] U.S. Cl. ...................................... 260/966; 4/280; 4/945
[58] Field of Search .................... 260/966; 252/78.5

[56] References Cited

U.S. PATENT DOCUMENTS

| Re. 29,540 | 2/1978 | Randell et al. | 260/966 |
| 3,576,923 | 4/1971 | Randell et al. | 260/966 |
| 3,859,395 | 1/1975 | Terhune et al. | 260/966 |
| 3,867,298 | 2/1975 | Malec | 260/966 |
| 3,919,158 | 11/1975 | Randell et al. | 260/966 |
| 4,093,680 | 6/1978 | Randell et al. | 260/966 |
| 4,096,209 | 6/1978 | Randell et al. | 260/966 |
| 4,139,487 | 2/1979 | Garrett | 260/966 |

*Primary Examiner*—Anton H. Sutto
*Attorney, Agent, or Firm*—Howard K. Kothe

[57] ABSTRACT

Tertiary-butylphenyl diphenyl phosphate esters in which the nominal molar ratio of tertiary-butyl radicals to phenyl radicals ranges from about 1:5 to about 1:2, the meta-tertiary-butylphenyl content ranges from about 25% to about 100 % and the ortho-tertiary-butylphenyl content is less than about 50% are highly effective plasticizers for vinyl chloride polymer compositions.

3 Claims, No Drawings

META-TERTIARY-BUTYLPHENYL DIPHENYL PHOSPHATE

This is a division, of application Ser. No. 091,633 filed Nov. 5, 1979 now U.S. Pat. No. 4,280,945.

BACKGROUND OF THE INVENTION

The present invention relates to plasticized vinyl chloride polymer compositions. More particularly, the present invention relates to vinyl chloride polymer compositions plasticized with meta-tertiary-butylphenyl diphenyl phosphate.

Various phosphate esters are known to be useful as plasticizers for vinyl chloride polymer compositions. One of the first phosphate esters recognized as being useful for this purpose was tricresyl phosphate. The relatively short supply of cresols, from which tricresyl phosphate is prepared however, made it necessary to develop alternative plasticizers. One such alternative was tri(2-ethylhexyl)phosphate. This compound imparted a low temperature flexibility to polyvinyl chloride which was even better than that imparted by tricresyl phosphate, but, unfortunately, the permanence of this plasticizer is less than desirable.

Another ester suggested as being a suitable substitute for tricresyl phosphate, is a phosphate ester disclosed in U.S. Pat. No. 3,931,091 and represented by the structural formula $(C_6H_5)_x(m\text{-}C_2H_5C_6H_4)_yPO_4$ wherein x is 1 or 2 and y is 1, 2 or 3 and the sum of x and y is 3. These phosphate esters, which contain at least one m-ethylphenyl group, are said to provide outstanding low temperature flexibility.

More recently it has been disclosed, in U.S. Pat. No. 4,139,487; that the presence of alkyl substituents in at least one of the aryl groups of triaryl phosphates provides improved performance of the triaryl phosphates as plasticizers for vinyl chloride polymers, particularly with respect to low temperature flexibility. The patent teaches that the presence of an isopropyl or sec-butyl group is particularly advantageous and that the presence of alkylphenyl groups containing tertiary carbon atoms is less preferred. Meta-isopropylphenyl diphenyl phosphates are mentioned as being most preferred.

While the state-of-the-art has developed to a point where plasticizers are now available which are relatively effective, a tremendous growth in the use of vinyl chloride polymer compositions and the development of new fields of application for the same presents a need for new plasticizers which are even more effective than those presently available.

SUMMARY OF THE INVENTION

It has now been found that tertiary-butylphenyl diphenyl phosphate esters in which the nominal molar ratio of tertiary-butyl radicals to phenyl radicals ranges from about 1:5 to about 1:2, the meta-tertiary-butylphenyl portion of the total tertiary-butylphenyl content ranges from about 25% to 100% and the ortho-tertiary-butylphenyl content is less than about 50% are highly effective plasticizers for vinyl chloride polymer compositions.

In accordance with the present invention there is provided a plasticized vinyl chloride polymer composition comprising a vinyl chloride polymer and a plasticizingly-effective amount of a tertiary-butylphenyl diphenyl phosphate having a nominal molar ratio of tertiary-butyl radicals to phenyl radicals ranging from about 1:5 to about 1:2 and wherein the meta-tertiary-butylphenyl portion of the total tertiary-butylphenyl content ranges from about 25% to about 100% and the ortho-tertiary-butylphenyl content is less than about 50%.

The plasticized vinyl chloride polymer compositions of the present invention are formed by adding the plasticizer to vinyl chloride polymers.

The vinyl chloride polymers which are used in forming the vinyl chloride compositions of the present invention are well known in the art. These materials include polymers produced not only by polymerizing vinyl chloride monomer to produce polyvinyl chloride homopolymer, but also those formed by copolymerizing vinyl chloride monomer with other ethylenically unsaturated aliphatic monomers having molecular weights generally under about 260 which are copolymerizable with vinyl chloride to produce polyvinyl chloride. Such comonomers include olefins, such as ethylene, propylene and the like; vinyl ethers (e.g., vinyl ether, 2-ethylhexyl vinyl ether, benzyl vinyl ether, etc.); vinylidene chloride; alkyl acrylate esters in which the alkyl group contains 1 to 20 carbon atoms (e.g., methyl acrylate, butylacrylate, octadecyl acrylate, etc.) and the corresponding alkyl methacrylate esters; and dialkyl esters of dibasic organic acids in which the alkyl groups contain 2 to 8 carbon atoms (e.g., dibutyl fumarate, diethyl maleate, etc.).

Preferred vinyl chloride polymers have chlorine contents ranging from about 45.0 to about 56.7% and have molecular weights such that a 0.4% by weight solution of such polymer in cyclohexanone at 25° C. has a specific viscosity of from about 0.3 to about 0.6. More preferred specific viscosities range from about 0.4 to about 0.5. A preferred class of vinyl chloride polymer is polyvinyl chloride homopolymer. In general, one should choose a vinyl chloride polymer for use in the present invention which will offer most satisfactory properties in a particular desired end product, e.g., a heat fused sheet or film product.

The tertiary-butylphenyl diphenyl phosphate ester of the present invention is added to the vinyl chloride polymer in a plasticizingly-effective amount. The amount required to be plasticizingly-effective generally ranges from about 10 to about 70 weight parts per hundred parts of vinyl chloride polymer.

Although the plasticizer of the present invention is referred to herein as meta-tertiary-butylphenyl diphenyl phosphate, it is not a true meta-tertiary-butylphenyl diphenyl phosphate because the actual molar ratio of the alkylphenyl to phenyl moieties is not always 1 to 2, (i.e., a molar ratio of tertiary-butyl to phenyl of 1:3) although this ratio is preferred. The molar ratio of alkyl moiety to phenyl moiety in the phosphate ester plasticizer of the present invention can actually range from about 1:5 to about 1:2.

In the plasticizer of the present invention, the percentage of tertiary-butylphenyl which is in the meta-isomer form can vary from about 25% to about 100%, although a range of from about 45% to about 80% is preferred.

The phosphate ester plasticizer of the present invention can be prepared by phosphorylating an appropriate alkylphenol mixture.

One preferred appropriate alkylphenol mixture is that which is at least 90% phenol, meta-tertiary-butylphenol and para-tertiary-butylphenol; and in which the molar ratio of meta-tertiary-butylphenol to para-tertiary-butylphenol ranges from about 1:1 to about 3:1, and the molar ratio of tertiary-butyl to total phenyl (i.e., free phenol and alkylphenol) ranges from about 1:5 to about 1:2.

There are many methods known to those skilled in the art by which the alkylphenol mixtures can be prepared. One preferred method is that taught by U.S. Pat. No. 4,103,096. In accordance with that patent, an olefin, such as isobutylene is reacted with phenol in the presence of trifluoromethane sulfonic acid at elevated temperatures to form an alkylphenol reaction mixture, and then the reaction mixture is maintained at an elevated temperature for a time sufficient to convert non-meta-isomer components of the mixture to meta-isomer. When employing this method, the relative amount of isobutylene and phenol charged should be consistent with the molar ratios stated above, and the reaction conditions should be maintained for a period of time sufficient to obtain the meta-to-para-ratios discussed above. Generally, this can be accomplished in a period of time ranging from about 2 to about 20 hours, depending on the temperature and the amount of trifluoromethane sulfonic acid used.

An optional ingredient in the plasticizer composition can be a secondry plasticizer such as one of the esters of polyhydric alcohols such as pentaerythritol, sorbitol, mannitol, trimethylolpropane, and the like, with monobasic $C_1$–$C_{10}$ alkyl group containing acids, such as acetic, butyric and heptanoic acids; a phthalate ester of an aliphatic alcohol, such as 2-ethylhexanol, n-octanol, n-decanol, iso-octanol or iso-decanol; an aliphatic dibasic acid ester such as diisodecyl adipate or dibutyl sebacate; an isophthalate ester such as 2-ethylhexyl isophthalate; or a trimellitate, such as tris(2-ethylhexyl)-trimellitate. Generally, the amount used will range anywhere from about 5% to about 15%, by weight of the primary plasticizer.

In order that the present invention be more fully understood, the following examples are given by way of illustration. No specific details or enumerations contained therein should be construed as a limitation on the present invention except insofar as they appear in the appended claims.

EXAMPLE 1

Five alkylphenol/phenol mixtures were prepared by mixing together phenol, meta-tertiary-butylphenol and para-tertiary-butylphenol in varying ratios. In each case the alkyl to phenyl ratio for the overall mixture was maintained at 1:3, but the ratio of meta-tertiary-butylphenol to para-tertiary-butylphenol was varied from 100% meta-tertiary-butylphenol to 100% para-tertiary-butylphenol. Each of these mixtures was then phosphorylated with $POCl_3$ to form the corresponding phosphate ester. Each of the phosphate esters were then tested as plasticizers in a polyvinylchloride at concentrations of 50 parts per hundred parts of PVC. The results were as shown in Table I.

TABLE I

| Sample | PVC Physical Properties | | | | |
|---|---|---|---|---|---|
| | A | B | C | D | E |
| m/p Ratio | 1.0/0 | 0.75/0.25 | 0.50/0.50 | 0.25/0.75 | 0/1.0 |
| Tensile Str. kg/cm² | 214.09 | 221.82 | 219.30 | 218.73 | 219.37 |
| % Elongation | 233 | 263 | 245 | 229 | 217 |
| 100% Modulus kg/cm² | 164.24 | 170.57 | 176.34 | 177.25 | 189.98 |
| Shore "A" Hardness | | | | | |
| 10 sec. | 87 | 90 | 90 | 95 | 95.5 |
| Clash Berg, °C. | +1 | +4 | +5 | +5 | +11 |

The tensile strength at break is the maximum tensile stress sustained by a specimen during a tension test (ASTM D-882). The result is expressed in kg/cm² with the area being that of the original specimen at point of rupture.

Percent elongation of break is the increase in distance between two gauge marks on the specimen at rupture (ASTM C-882) divided by the original distance between the marks, the quotient being multiplied by 100.

Shore "A" hardness is a measure of indentation hardness and is determined on the Shore A durometer after 10 seconds (ASTM D-2240). This instrument comprises a spring loaded indentor point with a load of 822 grams projecting through a hole in a presser foot. The device has a scale which indicates the degree of penetration into the plastic beyond the face of the foot. The scale ranges from 0 (for 0.254 cm. penetration) to 100 (for zero penetration).

The Clash-Berg point is the temperature at which the apparent modulus of elasticity of the spcimen is 9491.4 kg/cm² and is the end of flexibility of the sample as defined by Clash and Berg in their studies of low temperature flexibility. Lower values indicate a sample having a superior degree of low temperature flexibility.

As can be seen from the tabulated data, the overall effectiveness improved as the meta-to-para ratio increased in accordance with the present invention.

EXAMPLE 2

Five different alkylphenol mixtures were prepared by the reaction of isobutylene with phenol in the presence of trifluoromethane sulfonic acid. Each of the alkylphenol mixtures was then phosphorylated with $POCl_3$ and tested as a PVC plasticizer at a concentration of 50 parts per hundred parts of PVC. The composition of the alkylphenol samples, the properties of the resulting esters and properties of the PVC composition prepared with each ester are shown in Table II.

TABLE II

| Properties of Esters Prepared From Tertiary-butyl/phenol Mixtures | | | |
|---|---|---|---|
| | Sample | | |
| | F | G | H |
| A. TBP Composition | | | |
| Phenol | 63.4 | 56.7 | 67.2 |
| Ortho-tertiary-butylphenol | 0 | 0.9 | 0.4 |
| Meta-tertiary-butylphenol | 24.5 | 32.2 | 17.9 |
| Para-tertiary-butylphenol | 8.3 | 11.1 | 14.6 |
| Meta/(meta + para) % | 74.7 | 74.4 | 55.1 |
| 2,4-ditertiary-butylphenol | 0 | 0 | — |
| 2,6-ditertiary-butylphenol | 0 | 1.2 | — |
| 2,5–3,5-ditertiary-butylphenol | 2.41 | 0 | — |
| Unknown | 0 | 0.2 | — |
| $C_4/\phi$ | 0.27 | 0.34 | 0.22 |
| B. Ester Properties | | | |
| $n_D^{25}$ | 1.5520 | 1.5510 | 1.5540 |

TABLE II-continued

Properties of Esters Prepared From Tertiary-butyl/phenol Mixtures

|  | Sample | | |
| --- | --- | --- | --- |
|  | F | G | H |
| $d_{25}$ | 1.16 | 1.16 | 1.15 |
| Acid No. | 0.10 | 0.10 | 0.10 |
| APHA | 25 | 15 | 50 |
| SUS/(37.8° C.) | — | 138 | — |
| C. PVC Plasticizer Properties | | | |
| Tensile Str. (kg/cm$^2$) | 228.72 | 221.82 | 232.16 |
| Elongation (%) | 235 | 255 | 239 |
| 100% Modulus (kg/cm$^2$) | 164.95 | 164.03 | 169.31 |
| Shore A Hardness | 86.5 | 86 | 87 |
| Clash-Berg (°C.) | 0 | +1.5 | 0 |
| A. TBP Composition | | | |
| Phenol | 68.8 | 57.8 | 68.9 |
| Ortho-tertiary-butylphenol | — | 0.61 | 0 |
| Meta-tertiary-butylphenol | 23.0 | 30.8 | 21.9 |
| Para-tertiary-butylphenol | 6.7 | 10.5 | 8.3 |
| Meta/(meta + para) % | 77.4 | 74.6 | 72.5 |
| 2,4-ditertiary-butylphenol | — | 1.3 | 0 |
| 2,6-ditertiary-butylphenol | — | 0 | 0 |
| 2,5-3,5-ditertiary-butylphenol | 0.8 | 0 | 0 |
| Unknown | 0.5 | 0.4 | 0 |
| $C_4/\phi$ | 0.23 | 0.32 | 0.22 |
| B. Ester Properties | | | |
| $n_D^{25}$ | 1.5505 | 1.5517 | 1.5550 |
| $d_{25}$ | 1.15 | 1.15 | 1.15 |
| Acid No. | 0.10 | 0.10 | 0.10 |
| APHA | 75 | 15 | 10 |
| SUS/(37.8° C.) | — | 140 | — |
| C. PVC Plasticizer Properties | | | |
| Tensile Str. (kg/cm$^2$) | 231.04 | 225.70 | 227.87 |
| Elongation (%) | 261 | 275 | 269 |
| 100% Modulus (kg/cm$^2$) | 165.65 | 165.65 | 161.43 |
| Shore A Hardness | 88 | 87 | 86 |
| Clash-Berg (°C.) | +2 | 0 | +3.0 |

These results demonstrate that the high meta-isomer-containing tertiary-butylphenyl diphenyl phosphate esters of the present invention are superior plasticizers for vinyl chloride compositions.

It will thus be seen that the meta-isomer tertiary-butylphenyl diphenyl phosphate esters of the present invention provide effective plasticizers for vinyl chloride compositions.

What is claimed:

1. A plasticizer for vinyl chloride polymer compositions comprising a tertiary-butylphenyl diphenyl phosphate having a nominal molar ratio of tertiary-butyl radicals to phenyl groups ranging from about 1:5 to about 1:2 and wherein the meta-tertiary-butylphenyl portion of the total tertiary-butylphenyl content ranges from about 25% to about 100% and the ortho-tertiary-butylphenyl content is less than about 50 mole %.

2. The plasticizer of claim 1 wherein said nominal molar ratio of tertiary-butyl radicals to phenyl radicals is 1:3.

3. The plasticizer of claim 2 wherein the meta-tertiary-butylphenol portion of total tertiary-butylphenyl ranges from about 45% to about 80%.

* * * * *